(12) United States Patent
Swartz

(10) Patent No.: US 6,218,395 B1
(45) Date of Patent: *Apr. 17, 2001

(54) CENTRALLY-ACTING BETA-BLOCKERS AND SEROTONIN-ENHANCERS FOR THE TREATMENT OF ANXIETY DISORDERS AND ADJUSTMENT DISORDERS WITH ANXIETY

(76) Inventor: Conrad Melton Swartz, 1215 McCutcheon Ave., Richmond Heights, MO (US) 63117

( * ) Notice: Subject to any disclaimer, the term of this patent is extended or adjusted under 35 U.S.C. 154(b) by 0 days.

This patent is subject to a terminal disclaimer.

(21) Appl. No.: 09/366,130

(22) Filed: Aug. 2, 1999

(51) Int. Cl.[7] .......................... A61K 45/06; A61K 31/135
(52) U.S. Cl. ........................ 514/252.15; 514/652
(58) Field of Search ................... 514/252.15, 652

(56) References Cited

U.S. PATENT DOCUMENTS

| 4,182,763 | * | 1/1980 | Casten et al. | 424/251 |
|---|---|---|---|---|
| 5,525,347 | * | 6/1996 | Kellner et al. | 514/406 |
| 5,798,393 | * | 8/1998 | Swartz | 514/652 |
| 5,922,341 | * | 7/1999 | Smith et al. | 424/430 |
| 5,958,429 | * | 9/1999 | Wong, I | 424/400 |

FOREIGN PATENT DOCUMENTS

| 0 759299A1 | * | 2/1997 | (EP) . |
| 0 792649A1 | * | 9/1997 | (EP) . |

OTHER PUBLICATIONS

Buspar (Buspirone HCL, USD) Bristol–Myers Squibb (Patient Instruction Sheet How To Use) Indicated For The Management Of Anxiety Disorders/Short Term Relief Of Symptoms of Anxiety, May 1998.*

* cited by examiner

Primary Examiner—Shep K. Rose
(74) Attorney, Agent, or Firm—Eliot Gerber

(57) ABSTRACT

A combination of medicines are administered daily for the relief of the symptoms of an Anxiety Disorder or an Adjustment Disorder With Anxiety. The combination comprises a centrally-acting beta-blocker which passes the brain blood barrier, preferably the beta-blocker betaxolol, and a serotonin-enhancer, for example, the serotonin agonist buspirone or the serotonin reuptake inhibitor sertraline.

9 Claims, No Drawings

CENTRALLY-ACTING BETA-BLOCKERS AND SEROTONIN-ENHANCERS FOR THE TREATMENT OF ANXIETY DISORDERS AND ADJUSTMENT DISORDERS WITH ANXIETY

FIELD OF THE INVENTION

The present invention relates to medicine and more particularly to the administration of pharmaceuticals to relieve anxiety disorders and adjustment disorders with anxiety.

BACKGROUND OF THE INVENTION

Anxiety disorders are common, and they pose discomfort and health risks to the person who suffers with symptoms, his family and his co-workers.

The term "anxiety disorders" refers here to the group of conditions which are long-standing and persistent. They are listed under this term in the Diagnostic and Statistical Manual of Psychiatry, Fourth Edition. The presently accepted names of such anxiety disorders are: Generalized Anxiety Disorder, Obsessive-Compulsive Disorder, Post-Traumatic Stress Disorder, Acute Stress Disorder, Panic Disorder, Agoraphobia, Specific Phobia, Social Phobia, Anxiety Disorder Due to General Medical Condition, Substance-Induced Anxiety Disorder, and Anxiety Disorder Not Otherwise Specified. These "anxiety disorders" are different from ordinary "reactive anxiety" which occurs in the normal course of life, for example, due to the stress of moving from one house to another. Such reactive anxiety disorders, without medication, decrease with time, e.g., in one to four weeks.

The term "adjustment disorders with anxiety" refers to conditions listed under this term in the cited Diagnostic and Statistical Manual of Psychiatry, which include the expression of anxiety. These conditions are: Adjustment Disorder with Anxiety, Adjustment Disorder with Mixed Anxiety and Depressed Mood, and Adjustment Disorder with Mixed Disturbance of Emotions and Conduct, in which the emotional symptoms include anxiety.

The term "centrally-acting beta-blockers" as used herein encompasses medications that enter the central nervous system by passage from the bloodstream across the blood-brain barrier, and there block beta-adrenergic receptors. This blockade of beta-adrenergic receptors may provide reliable therapeutic benefits for anxiety disorders, for example, the use of the beta-blocker betaxolol, as described in U.S. Pat. No. 5,798,393 (Swartz 1998). Not all beta-blockers are "centrally-acting beta-blockers" since some do not cross the blood-brain barrier, i.e., atenolol and nadolol.

The medications which have been identified as centrally-acting beta-blockers are: acebutolol, betaxolol, bisopropolol, bopindolol, carvedilol, metoprolol, oxprenolol, propranolol, and timolol. Those beta-blockers include, for each, its racemic mixture, its optical isomer, its immediate-release and sustained-release preparation. Generally, beta-blockers are not recognized by psychiatrists as a medication to treat anxiety disorders.

The term "serotonin-enhancer", as used herein, means medications that increase or prolong serotonergic neurotransmission. For example, they act as a counteraction, an agonist of serotonin at serotonin receptor sites; by preventing the degradation of serotonin, by increasing the formation of serotonin, by preventing the removal of serotonin from the sites (i.e., the synaptic cleft) of the serotonin-reuptake inhibitor (SRI), by prolonging the actions or effects of serotonin, or by diminishing influences that inhibit serotonin release (Lakoski and Aghajanian 1985). Serotonin agonists include buspirone (BuSpar™) gepirone, and ipsapirone. Serotonin precursors, which increase its formation, include L-tryptophan and 5-hydroxytryptophan (5-HTP). Serotonin reuptake inhibitors (SRI) include chlorimipramine (also known as clomipramine and chlorimipramine), citalopram, fluoxetine (Prozac™), fluvoxamine, paroxetine, sertraline, venlafaxine, lamotrigine, and carbamazepine. Agents which diminish influences that inhibit serotonin release include presynaptic serotonin antagonists, which include ritanserin, ketanserin, risperidone, mirtazepine, nefazodone, trazodone, olanzapine, clozapine, serazepine, methysergide, mianserin, and flibaserin. Each agent includes its racemic mixture, optical isomer, immediate-release preparation and sustained-release preparation.

Separately, several centrally-acting beta-blockers and several serotonin enhancers have been identified as providing benefits in the mitigation of anxiety and in the treatment of anxiety disorders.

Benefits in the mitigation of anxiety and in the treatment of anxiety disorders have been reported for several centrally-acting beta blockers (e.g. Swartz 1998; Meibach et al 1987) and several serotonin enhancers (Michaelson et al 1998; Ballenger et al 1998).

SUMMARY OF THE INVENTION

As a combination of two different and complementary actions to mitigate anxiety disorders, the administration of a beta-blocker together with a serotonin-enhancer is believed to be more effective than either medication used alone. If they are administered together, they provide a synergistic effect—their combination provides a beneficial effect which is greater than would be expected on a dosage basis. The reason for this greater-than-additive effect is that somatic anxiety and psychic anxiety each provoke and exacerbate the other, and the mitigation of both together augments the mitigation of each. In the mitigation of anxiety, a beta-blocker primarily mitigates somatic anxiety, and this variably leads to a secondary mitigation of psychic anxiety. In the mitigation of anxiety, a serotonin-enhancer primarily mitigates psychic anxiety, and this leads to a secondary mitigation of somatic anxiety. Moreover, because the side effects of serotonin-enhancers include the symptoms of somatic anxiety, beta-blockers mitigate the side effects of serotonin-enhancers.

DETAILED DESCRIPTION OF THE INVENTION

Anxiety disorders are common; without including Adjustment Disorders, their 12-month prevalence is about 13% (Kessler et al 1994). Their recognition and treatment is urgent, not only because of psychological suffering but because anxiety can lead to sudden death, cardiac injury, or suicide (Kawachi et al, 1994a,1194b; Ketterer, 1997; taker et al 1992; Fawcett et al 1987; Chance et al 1994). A basic use of serotonin-enhancers is the mitigation of anxiety disorders, of mild to mild-to-moderate severity, in patients for whom symptoms are primarily psychic anxiety, e.g., persistent worry, doubt, dread, repetitive thoughts or obsessionalism, repetitive behavior or compulsiveness, mental concentration difficulty, and mood instability. In persistent, or more severe, cases somatic anxiety symptoms develop and add to the difficulty of achieving relief. Somatic anxiety symptoms include agitation, restlessness, jumpiness, edginess, hyperalertness, initial insomnia, vivid dreams, chest tightness, palpitations, irritable bowels, dyspepsia, headaches, dyspnea, and panic attacks. Somatic anxiety symptoms provoke and exacerbate psychic anxiety symptoms, and vice-versa, which produces a "positive feedback" cycle. In the natural progression of anxiety disorders, in time and in severity, psychic anxiety irritates somatic anxiety, which irritates more psychic anxiety, which irritates more somatic anxiety, and so forth. Several symptoms result from a combination of somatic anxiety and psychic anxiety, such as mind-blanking, irritability, argumentativeness, nightmares, and aggressive or violent behavior. Further, somatic anxiety symptoms are the same symptoms which are common side effects of serotonin-enhancers, and somatic anxiety symptoms and these side effects can provoke and exacerbate each other.

Patients with anxiety disorders who visit psychiatrists usually have somatic anxiety symptoms. This is probably because by the time a patient is referred to a psychiatrist, or is willing to see one, the disorder has become persistent and of substantial severity. Perhaps because of the somatic anxiety symptoms, improvements by patients with post-traumatic stress disorder (PTSD) on serotonin-enhancers alone is often incomplete and slow, and side-effects are often problematic. Serotonin-enhancers are better tolerated by and more effective in patients who do not have somatic anxiety symptoms.

The blockade of beta-adrenergic receptors decreases the effects of internal secretions of the hormone epinephrine (also called adrenaline) and related hormones, which activate this receptor. Cells in the central nervous system (CNS) which contain epinephrine stimulate the activation of the sympathetic nervous system; these cells contain much more epinephrine than serotonin or other neurotransmitter chemicals (Jansen et al 1995). Activation of the sympathetic nervous system increases alertness and energy, but excessive activation induces feelings of panic, fear, anxiety, or anger. This blockage decreases unpleasant bodily sensations associated with anxiety, fear, and stress, which can be further irritating and stressful to patients. Decrease in these somatic symptoms is one of the two mechanisms through which beta-blockers, in the present invention, are anticipated to be effective in PTSD and other anxiety disorders. The other mechanism is a decrease in the activity of the areas in the central nervous system which mediate and express anxiety and which activate the sympathetic nervous system.

Recent experimental observations in laboratory animals revealed that the brain cells which activate the sympathetic nervous system—and thereby express the somatic manifestations of anxiety—contain a substantial amount of neurotransmitter epinephrine (Jansen et al 1995), a neurotransmitter which potently activates beta-adrenergic receptors. This indicates the central role of epinephrine and beta-adrenergic receptors in the expression of somatic anxiety symptoms. This same study found these same brain cells to also contain some serotonin. It is the inventor's reasoning that the inclusion of serotonin in these cells indicates that serotonin also provokes the activation of these cells, thereby causing somatic manifestations of anxiety. Accordingly, decreasing the activity of these cells by decreasing their reactivity to epinephrine should counteract their activation by serotonin-enhancers and improve the tolerability and effect of serotonin-enhancers.

Although centrally-acting beta-blockers may help to prevent side-effects from serotonin-enhancers, when both are started at the same time, such beta-blockers are more effective at such prevention when their administration precedes the serotonin-enhancer. This is because such advance administration allows such beta-blocker's absorption, distribution, propagation, and development of its pharmacologic effects, to occur and function throughout the period of the patient's exposure to the serotonin-enhancer. In this way, the side-effects of the serotonin-enhancer are milder or non-existent due to the preventive effects of the centrally-acting beta-blocker. Accordingly, both simultaneous and advance administration of such beta-blockers are included here.

Betaxolol is the preferred beta-blocker among the beta-blockers that enter the brain because it is eliminated relatively slowly. Because of such slow elimination, betaxolol gives consistent effects throughout the day and night without the rebound effects. A once-daily dosing of betaxolol and a serotonin-enhancer may produce better compliance than using short-acting drugs which require more frequent dosing.

Although betaxolol is the preferred centrally acting beta-blocker, others, such as metoprolol and propranolol, may prove to be useful. Betaxolol hydrochloride ("betaxolol"™) blocks beta-adrenergic receptors on cell membranes in the body, i.e., it is a beta-blocker. Betaxolol is largely specific to subtype 1 of beta-adrenergic receptors. The chemical name of betaxolol is:

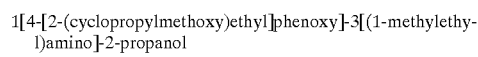

and includes its pharmaceutically acceptable acid addition salts, preferably the addition salt of hydrochloride. Its molecular formula is $C_{18}H_{29}NO_3$ HCl. It is a white crystalline powder that is soluble in water and ethanol. It is available from ALCON LABORATORIES, Fort Worth, Tex., U.S.A., and Kayersberg, France.

Our tests have shown that the beta-blocker betaxolol and a serotonin-enhancer ("the combination") has the following advantages:

1. The combination relieves anxiety and panic symptoms faster than other antidepressants. For example, it may work in 1 to 3 days, compared to 2–12 weeks or longer. Such faster response may permit shorter hospital stays, less time needed from doctors, more rapid relief and greater attractiveness to the patient with consequent better compliance with the prescribed dosage.

2. The betaxolol has rapid cardioprotective action in patients with anxiety-induced arrhythmia or coronary artery spasm. Although benzoodiazepine sedatives can temporarily provide this benefit, they have the potential for abuse. In addition, benzodiazepine sedatives lose effectiveness after a few weeks as a result of tolerance by the body and may cause impairment of cognitive function or physical performance.

3. When given by themselves, SRI antidepressants often provide undesirable adverse side effects, including nausea, headache, diarrhea and intestinal spasms, interference with sexual function and drowsiness. These are worse at higher doses. It may be possible to reduce the dosage of the SRI, in the combination with betaxolol, and thereby reduce such adverse side effects.

4. MAO-inhibitors may cause blood pressure elevation or tachycardia. However, we have seen no such risk of dangerous blood pressure elevation using the betaxolol and serotonin-enhancer combination. Indeed, beta-blockers decrease blood pressure.

5. Tricyclic antidepressants may have adverse anticholinergic effects, including urinary retention, dry mouth, glaucoma, tachycardia and constipation. No such adverse effects were found using the betaxolol and serotonin-enhancer.

EXAMPLES

The combination of a beta-blocker and a serotonin-enhancer was used, with a variety of patients suffering from an anxiety disorder or an adjustment disorder with anxiety. With each patient, clinical experience and follow-up revealed substantial benefit from this combination of medications.

Patient #1

At the time of psychiatric hospitalization this 51-year-old married Caucasian female complained of "severe anxiety" which had been a problem for about 30 years. She worried constantly, was easily upset by small things, her endurance was low and she easily ran out of energy. Her restlessness prevented her from sleeping well, and her mind so often went blank it interfered with her activities. She complained of "extreme pain" throughout her abdomen for three months, with troublesome nausea, vomiting, diarrhea, and headaches. These stomach symptoms began when she started taking the serotonin-enhancer drug sertraline, 50 mg per day. These symptoms persisted as the sertraline dose was gradually increased to 225 mg daily. She believed that sertraline had no side-effects and could not be responsible for the nausea, diarrhea, and headaches. On interview, she spontaneously criticized many people, including previous doctors and her husband. She showed an obvious tremor, irritability, and hyperalertness. Her diagnoses were Generalized Anxiety Disorder, Obsessive-Compulsive Personality Disorder, and Irritable Bowel Syndrome resulting from both the Generalized Anxiety Disorder and the serotonin-enhancer sertraline. The sertraline was stopped, and the abdominal discomfort disappeared, although the headaches continued. She was started on betaxolol, and the dose raised to 10 mg twice daily; a different kind of medication she was taking to control her blood pressure was stopped. In response to betaxolol her hyperalertness and irritability disappeared, and she felt calm. Her friends and family at home told her she looked strikingly different, and that she appeared healthier, more energetic, and calmer. About two weeks after starting betaxolol, and as an outpatient, buspirone was started while betaxolol was continued at 10 mg twice daily. The dose of buspirone was started at 5 mg three times daily and then increased to 10 mg three times daily. She had no gastrointestinal side-effects or other side-effects from the buspirone. After taking buspirone for a couple of weeks she described having a sense of happiness and satisfaction about herself and her life. The improvements were maintained over a five-month follow-up, during which time the betaxolol was increased to 20 mg twice daily; she did not develop anxiety symptoms, although during this time she separated from her husband and planned divorce.

Patient #2

This 52-year-old married Caucasian male stated that new job stresses caused problematic worry, restlessness, tremulousness, and jumpiness. The worry interfered with his concentration, and many times daily he felt dread. He had difficulty falling asleep and staying asleep because of the restlessness. He had daily heart palpitations, which annoyed and worried him, bowel spasms, and pressure headaches. He felt irritated by small matters which hadn't previously bothered him. He was diagnosed to have an Adjustment Disorder with Anxiety. In response to 2.5 mg of betaxolol twice daily, the tremulousness, restlessness, palpitations, and over-sensitivity disappeared, and he would occasionally sleep well. Worry and thoughts of dread continued. Two to three nights each week he would sleep 6 hours or more and feel rested and energetic. He engaged in regular arduous exercise and enjoyed friends and movies. Frequent worries and feelings of dread and discontent remained problematic; several times each day he found he could not stop worrying despite his resolve to stop. The betaxolol was continued and he started taking buspirone 5 mg three times daily. No side effects occurred, and within 12 hours of the first dose of buspirone he noticed that the worrying would stop with his resolve. On two or three occasions during the first week he found himself irritable, for up to half an hour, but after that there was no persistent or problematic worry or irritability. These benefits were maintained over a two-month follow-up.

Patient #3

This 47-year-old Caucasian male had a long history of psychiatric illness. He was first treated as having schizophrenia but was recently found to have bipolar manic-depressive disorder instead which responded well to valproic acid alone. He had long been living in institutions, and when the bipolar disorder recently remitted he began making frequent and vigorous resentful complaints about numerous small frustrations in his living environment. This friction caused his psychiatric hospitalization. In the hospital he was observed to spend most of the day agitatedly pacing a particular path rapidly and repeatedly. He fidgeted and tremored constantly, was easily irritated, and spoke in an impatient rapid staccato. He was given the diagnosis of Generalized Anxiety Disorder. He was started on betaxolol, 5 mg twice daily. In response to this agitation, irritability, tremulousness, and fidgeting were noticeably diminished, and he could hold a conversation without appearing irritated. He continued to pace and to express worry and disappointment about his living situation. The betaxolol was continued and buspirone 10 mg, three times daily, was started; no side effects appeared, despite the unusually large starting dose of buspirone. After one week he stopped pacing and complaining, and he sat calmly reading, watching television, or conversing. He consistently stated his expectation that things would work out fine in a group home. This serenity, poise, and optimism were striking changes in his persona. Observed in a day hospital program over the following month, the improvements were maintained.

Patient #4

This 41-year-old African American female was psychiatrically hospitalized, on her insistence, due to suicidality and excessive demands for attention to her complaints. She described a wide variety of worries in great length, detail and drama. She said she felt loss of control of her life and she claimed problematic feelings of abandonment, confusion, exhaustion, weakness, nervousness, jumpiness, hyperalertness, dizziness, and loss of morale over an 18-month period. She was easily upset by small things and often had tension headaches. She had difficulty maintaining attention and concentration, and difficulty falling asleep and staying asleep. At interview her hair was disarrayed and there was stubble on her face, doubly notable because she had been a cosmetologist. She fidgeted continuously in an agitated manner, and her mood oscillated rapidly and reactively between sadness and optimism. She was given the diagnoses of Generalized Anxiety Disorder and Obsessive-Compulsive Personality Disorder. On the first hospital day she was given betaxolol 5 mg and buspirone 5 mg together. Following this she described the new onset of several unpleasant sensations: hot flashes with sweating, an anxiety rush, and stomach pain. Buspirone was stopped on the second day, but the betaxolol was continued. She remained anxious and demanding, as before. On the fourth day the betaxolol dose was doubled to 10 mg. per day and buspirone was restarted, with 5 mg of each given twice daily. The hot flashes, sweating, anxiety rush, and stomach pain did not appear again. On the fifth day she showed only mild and transient agitation. By the seventh day the feelings of nervousness, confusion, exhaustion, jumpiness, and dizziness were gone, and she was sleeping well. Her mood was stable and she trimmed her nails, removed the facial stubble, and fixed her hair. On a follow-up phone call, two weeks later, her only complaint was of arthritis.

Patient #5

This 30-year-old Caucasian female nurse was hospitalized, after two months of anxiety and two weeks of panic attacks. Her panic attacks began two weeks after a spontaneous abortion which occurred seven weeks into pregnancy. The anxiety was manifested by hyperalertness, jumpiness, restlessness, difficulty falling asleep, difficulty focusing attention and concentration, weakness, nervousness, and obsessive worrying about death. The panic attacks included hyperventilation, shortness of breath, chest tightness, palpitations, and feelings of imminent death. Panic attacks often wakened her from sleep. On interview she was hyperalert and anxious, her mood varied rapidly, and she cried several times. She had failed to respond to individual trials of nefazodone, paroxetine with buspirone, and alprazolam. She was given the diagnoses of Generalized Anxiety Disorder, Panic Disorder, and Obsessive-Compulsive Personality Disorder. On the first hospital day she was started on betaxolol 5 mg daily and sertraline 50 mg daily. After the first dose, and while hospitalized, she did not have another panic attack. She slept soundly through the night. The next day she expressed fear that the panic would return and she cried several times. On the third day there were no crying spells. On the fourth day she felt calm and relaxed, and her mood was observed to be stable. On the sixth day she showed no distress, was not jumpy, and was not hyperalert. She smiled a great deal, showed consistent optimism, and denied depressed mood. On the eighth day she went home.

Patient #6

This 18-year-old African American female was psychiatrically hospitalized for irritability and demoralization from frustrations. She had a history of injuring other people and herself while enraged. She described restlessness, anger, impatience, irritability, tension headaches, jaw muscle tension, poor concentration, and difficulties falling asleep and staying asleep. She felt worried all the time, and was jumpy and easily upset. Her mood fluctuated repeatedly during the day. On interview she was hyperalert and she expressed emotions strongly. She was neatly groomed and dressed, and she spoke without hesitation, rapidly and to the point. At times she was optimistic and cheerful. She was given the diagnosis of Generalized Anxiety Disorder and started on betaxolol 5 mg/day on hospital day two. On day three she was no longer hyperalert or irritated and she did not speak rapidly. The jaw muscle tension was much decreased. Two doses of buspirone 5 mg were given, without any adverse effect. On day four she was calm, cheerful, and said she could manage her affairs well at home. She denied having any more thoughts to hurt others or herself.

ADMINISTRATION

The centrally-acting beta-blocker and the serotonin-enhancer, taken together or separately, either by itself or in combination with a carrier, may each be administered subcutaneously, intradermally, orally, parenterally, intraperitoneally, intravascularly, or by any other suitable means. The manner of administration will be selected in order to ensure that the drug or drugs are able to be directed to the site of desired action in an effective dosage. The centrally-acting beta-blocker and serotonin-enhancer may be combined into one pill or other forms of dosage.

Both the centrally-acting beta-blocker and the serotonin-enhancer may each be formulated in conventional manners employing a physiologically or pharmacologically acceptable carrier. Such carriers include solutions where the drug may be suspended (optionally employing a surfactant or emulsifier) or dissolved. The drug is available formulated as a tablet, capsule or the like. Orally administratable tablets and capsules containing from 5–95% active ingredient are suitable. Parenteral compositions containing 1–100 mg/ml can readily be prepared.

The dosage of the subject beta-blocker compounds varies with the particular compound. For betaxolol or bisopropol it will generally be at least about 1.0 and not more than about 40 mg per day in single or multiple doses, usually from about 3–20 mg/day and most preferably 4–12 mg/day. For propranolol or metoprolol it will generally be at least 20 and not more than about 240 mg per day in multiple doses. The treatment course can be given for a day, a few days, weeks, months, or years, depending upon the effectiveness of the course of treatment or the refractory nature of the disease.

The invention now being fully described, it will be apparent to one of ordinary skill in the art that many changes and modifications may be made thereto without departing from the spirit or scope of the appended claims.

What is claimed is:

1. A product for relieving the symptoms of Anxiety Disorder or Adjustment Disorder With Anxiety comprising, in a single dosage usage carrier an anxiolytically effective amount of a serotonin-enhancer and the centrally-acting beta blocker betaxolol.

2. A method of relieving the psychic and somatic symptoms of Anxiety Disorder or Adjustment Disorder with Anxiety consisting essentially of the step of daily coadministration of combined or concurrent anti-anxiety therapy of an anxiolytically effective amount of a serotonin-enhancer together with an anxiolytically effective amount of betaxolol, which is a centrally-acting long-acting non-serotonergic beta-blocker.

3. A product as in claim 1 wherein the serotonin-enhancer is selected from the group of serotonin agonists and serotonin reuptake inhibitors.

4. A product as in claim 3 wherein the serotonin-enhancer is buspirone.

5. A method as in claim 2 wherein the non-serotonergic beta-blocker betaxolol diminishes adverse side-effects of the serotonin-enhancer.

6. A method as in claim 2 wherein the serotonin-enhancer is selected from the group of buspirone, fluoxetine, paroxetine, sertraline, citralopram, fluvoxamine and venlafaxine.

7. A method as in claim 2 wherein the long-acting beta-blocker betaxolol is administered in the amount of 2–20 mg one to three times a day.

8. A method as in claim 7 wherein the serotonin-enhancer is selected from the group of serotonin agonists and serotonin reuptake inhibitors.

9. A method as in claim 7 wherein the serotonin-enhancer is of buspirone and sertraline.

* * * * *